(12) United States Patent
Baune (10) Patent No.: US 7,097,628 B1
(45) Date of Patent: Aug. 29, 2006

(54) TRACTION CHAIR SYSTEM

(76) Inventor: Robert D. Baune, Box 185, Morton, MN (US) 56270

( * ) Notice: Subject to any disclaimer, the term of this patent is extended or adjusted under 35 U.S.C. 154(b) by 142 days.

(21) Appl. No.: 10/892,081

(22) Filed: Jul. 14, 2004

(51) Int. Cl.
*A61F 5/00* (2006.01)

(52) U.S. Cl. .............. 602/32; 602/36; 602/19; 601/91; 297/464; 297/483

(58) Field of Classification Search .......... 602/19, 602/32, 36, 38, 33; 601/24, 91; 606/241, 606/242; 297/464–465, 468, 473, 483–486
See application file for complete search history.

(56) References Cited

U.S. PATENT DOCUMENTS

| | | | | |
|---|---|---|---|---|
| 951,560 | A | * | 3/1910 | Eaton ............... 602/32 |
| 1,356,365 | A | | 10/1920 | Hosmer |
| 2,803,245 | A | * | 8/1957 | Judovich ............ 602/32 |
| 2,828,735 | A | * | 4/1958 | Thompson .......... 602/32 |
| 3,567,283 | A | * | 3/1971 | Herbert ............. 297/410 |
| 3,975,051 | A | | 8/1976 | Ballagh ............. 297/434 |
| 4,207,879 | A | * | 6/1980 | Safadago et al. ..... 606/242 |
| 4,688,557 | A | | 8/1987 | Bradstreet .......... 128/71 |
| 4,858,919 | A | * | 8/1989 | Jones ................ 482/137 |
| 4,860,733 | A | | 8/1989 | Parker, Jr. ........... 128/25 |
| 4,981,148 | A | | 1/1991 | Fuller ............... 128/879 |
| 5,171,317 | A | | 12/1992 | Corcoran ............ 606/241 |
| 5,333,623 | A | | 8/1994 | Fuller ............... 128/875 |
| 5,380,269 | A | | 1/1995 | Urso ................ 602/19 |
| 5,437,609 | A | | 8/1995 | Leonard et al. ....... 601/91 |
| 5,848,984 | A | * | 12/1998 | Bachar et al. ........ 602/32 |
| 6,302,859 | B1 | * | 10/2001 | Cushman ............ 602/32 |
| 6,626,494 | B1 | * | 9/2003 | Yoo ................. 297/296 |
| 2003/0062750 | A1 | * | 4/2003 | Walter .............. 297/316 |

OTHER PUBLICATIONS

Chair with Mobile Traction Unit, Best-priced-products.com, Jun. 21, 2004, 1 Page.
TX Traction Units, Best-priced-products.com, Jun. 21, 2004, 2 Pages.
TX Traction Tables and Integrated table/treatment, Best-priced-products.com, Jun. 21, 2004, 2 Pages.
Hi-Lo Treatment Stool, Best-priced-products.com, Jun. 21, 2004, 1 Page.
Overdoor Cervical Traction, Best-priced-products.com, Jun. 21, 2004, 1 Page.
Saunders Cervical Traction, Best-priced-products.com, Jun. 21, 2004, 1 Page.
Saunders Home Trac Cervical Traction, Best-priced-products.com, Jun. 21, 2004, 1 Page.

* cited by examiner

*Primary Examiner*—Henry Bennett
*Assistant Examiner*—Amanda Wieker (57) ABSTRACT

A traction chair system for efficiently relieving an individual of lower back pain. The traction chair system includes a chair frame, a seat, a plurality of actuators attached between the chair frame and the seat for elevating/lowering the seat, a backrest, a harness attached to the backrest for securing an individual to the backrest, a motor mechanically elevating/lowering the backrest, and a control unit in communication with the actuators and the motor. A scale is positioned within the seat and in communication with the control unit for providing feedback to the individual regarding the actual amount of traction occurring. The amount of traction being applied to an individual is shown upon a display of the control unit.

19 Claims, 12 Drawing Sheets

TRACTION CHAIR SYSTEM

BACKGROUND OF THE INVENTION

1. Field of the Invention

The present invention relates generally to traction devices and more specifically it relates to a traction chair system for efficiently relieving an individual of lower back pain.

2. Description of the Related Art

Traction devices have been in use for years. A commonly utilized traction device is a harness structure that attaches about an individual's head and applies an upward force to the head thereby causing the pressure to be partially relieved from the individual's back.

While these devices may be suitable for the particular purpose to which they address, they are not as suitable for efficiently relieving an individual of lower back pain. Conventional traction devices do not directly relieve the pressure applied to the lower back of an individual because they focus upon relieving the pressure from the neck and upper back.

In these respects, the traction chair system according to the present invention substantially departs from the conventional concepts and designs of the prior art, and in so doing provides an apparatus primarily developed for the purpose of efficiently relieving an individual of lower back pain.

BRIEF SUMMARY OF THE INVENTION

In view of the foregoing disadvantages inherent in the known types of traction devices now present in the prior art, the present invention provides a new traction chair system construction wherein the same can be utilized for efficiently relieving an individual of lower back pain.

The general purpose of the present invention, which will be described subsequently in greater detail, is to provide a new traction chair system that has many of the advantages of the traction devices mentioned heretofore and many novel features that result in a new traction chair system which is not anticipated, rendered obvious, suggested, or even implied by any of the prior art traction devices, either alone or in any combination thereof.

To attain this, the present invention generally comprises a chair frame, a seat, a plurality of actuators attached between the chair frame and the seat for elevating/lowering the seat, a backrest, a harness attached to the backrest for securing an individual to the backrest, a motor mechanically elevating/lowering the backrest, and a control unit in communication with the actuators and the motor. A scale is positioned within the seat and in communication with the control unit for providing feedback to the individual regarding the actual amount of traction occurring. The amount of traction being applied to an individual is shown upon a display of the control unit.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a traction chair system that will overcome the shortcomings of the prior art devices.

A second object is to provide a traction chair system for efficiently relieving an individual of lower back pain.

Another object is to provide a traction chair system that may be utilized upon individuals of various heights, weight and sizes.

An additional object is to provide a traction chair system that capable of applying a traction force of approximately forty-percent of an individual's weight.

A further object is to provide a traction chair system that is simple to operate.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Turning now descriptively to the drawings, in which similar reference characters denote similar elements throughout the several views, FIGS. 1 through 9 illustrate a traction chair system 10, which comprises a chair frame 20, a seat 30, a plurality of actuators 40 attached between the chair frame 20 and the seat 30 for elevating/lowering the seat 30, a backrest 50, a harness 60 attached to the backrest 50 for securing an individual to the backrest 50, a motor 44 mechanically elevating/lowering the backrest 50, and a control unit 70 in communication with the actuators 40 and the motor 44. A scale 72 is positioned within the seat 30 and in communication with the control unit 70 for providing feedback to the individual regarding the actual amount of traction occurring. The amount of traction being applied to an individual is shown upon a display 71 of the control unit 70.

B. Chair Frame

Figure 1:
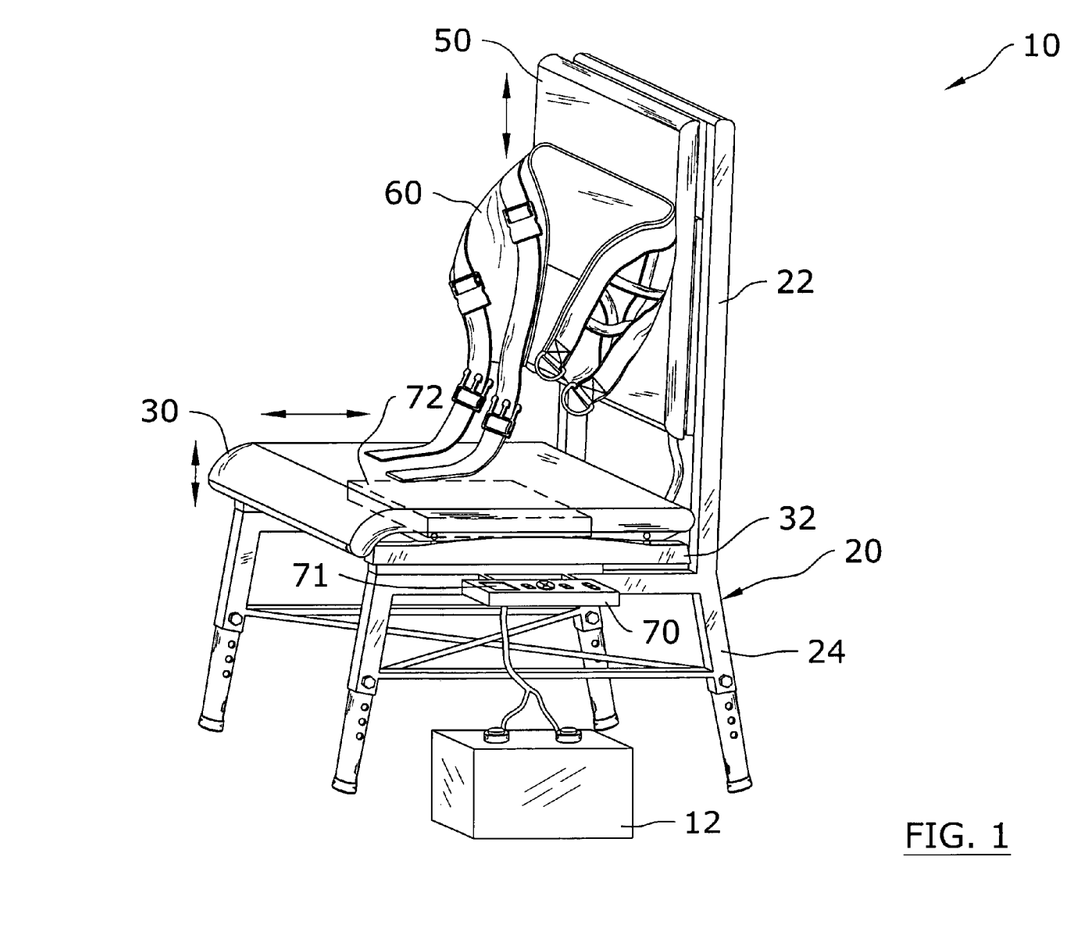
FIG. 1 is an upper perspective view of the present invention.
Figure 2:
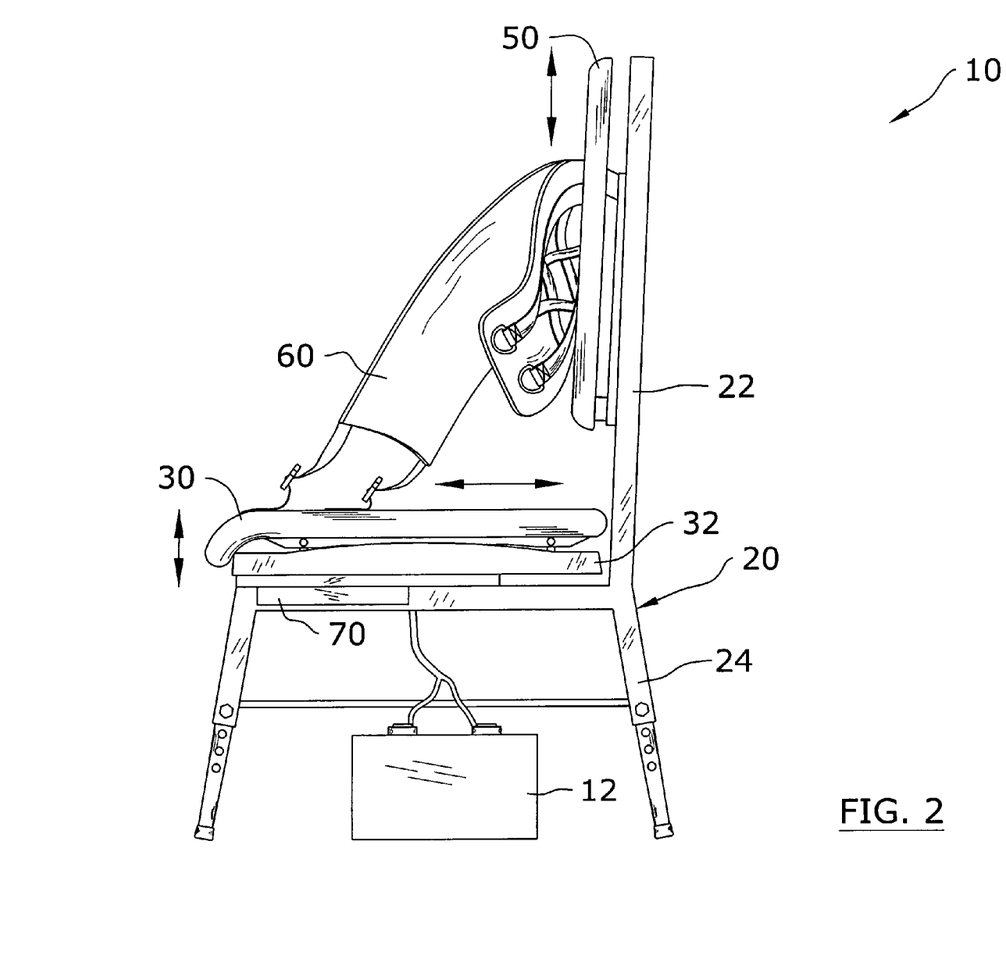
FIG. 2 is a side view of the present invention.

The chair frame 20 preferably has an upper frame 22 extending from a lower frame 24 as best illustrated in FIGS. 1 and 2 of the drawings. The lower frame 24 preferably includes a plurality of legs that may also be adjustable in length. The chair frame 20 may have various shapes and structures commonly utilized for chairs.

Figure 8A:
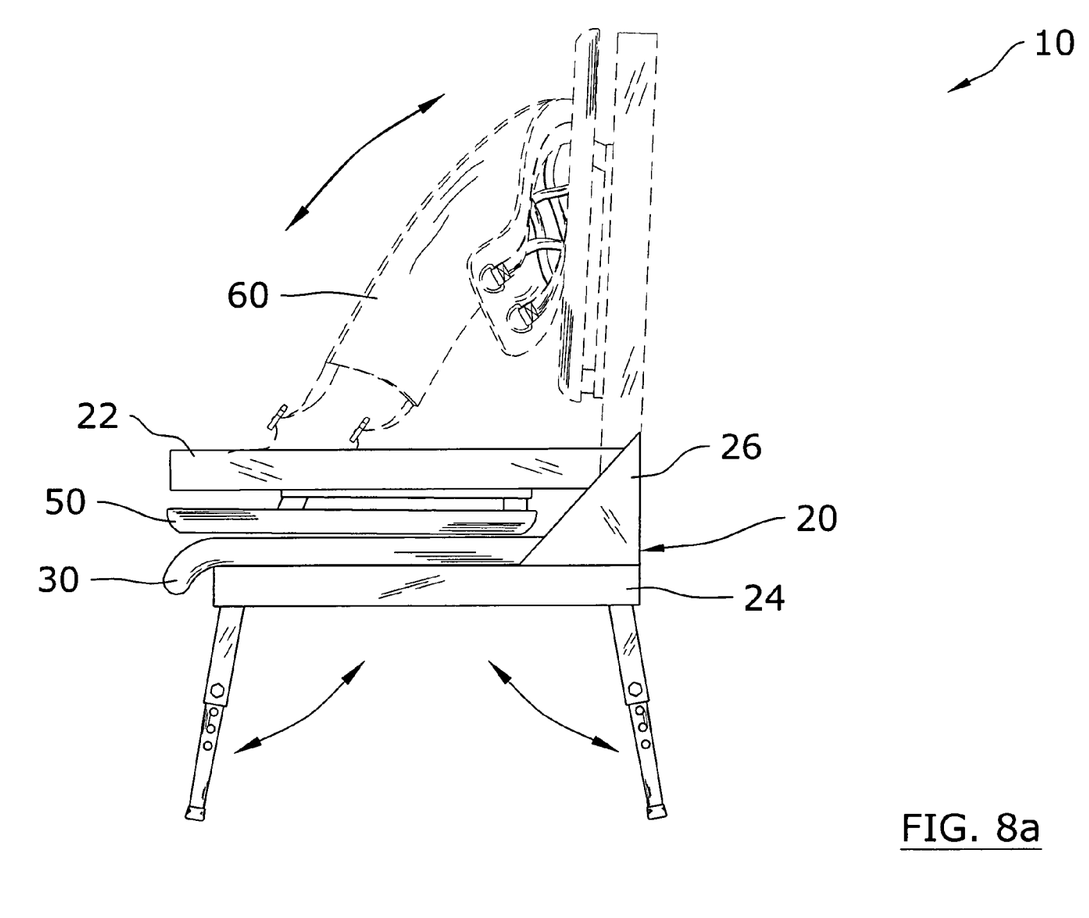
FIG. 8a is a side view of an alternative embodiment of the present invention illustrating the chair frame having a folding structure.
Figure 8B:
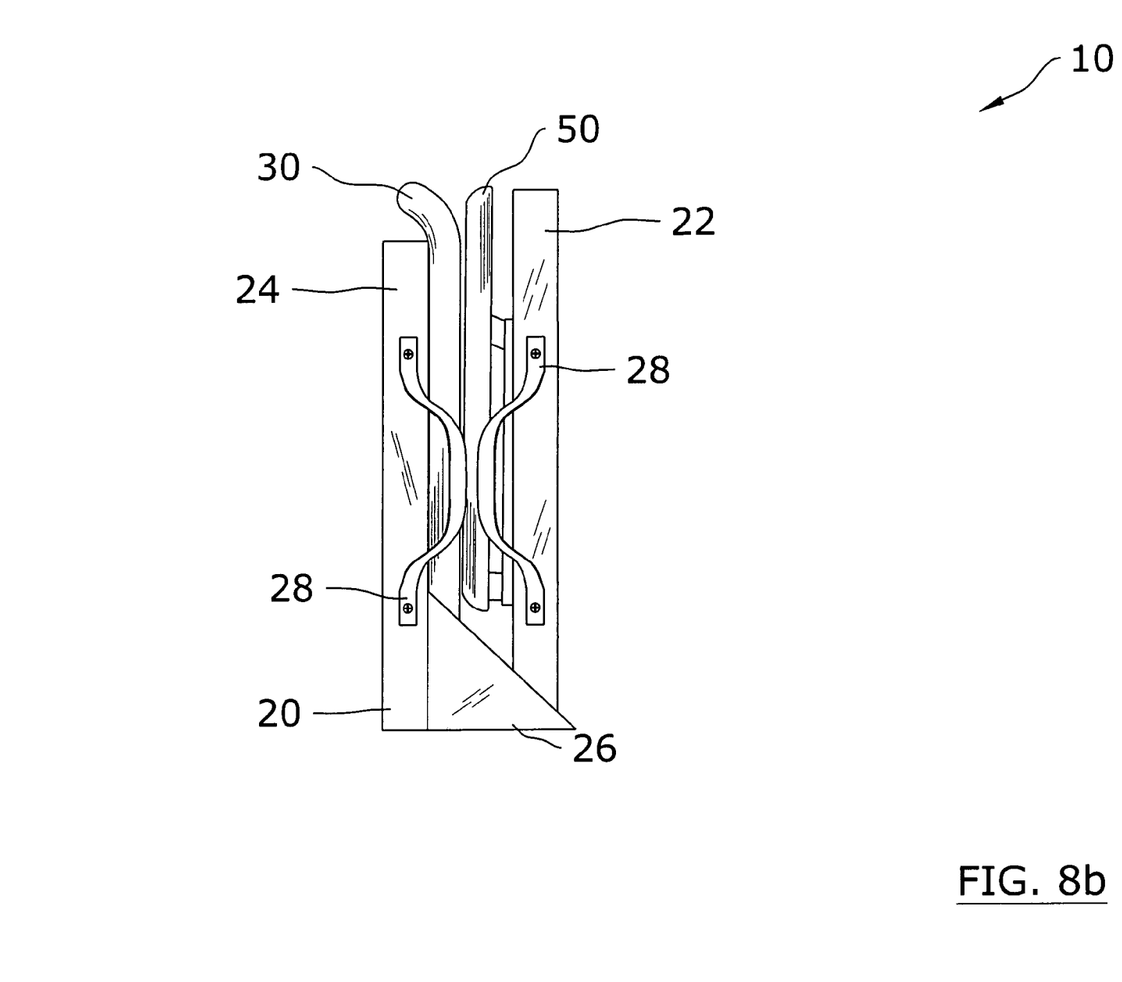
FIG. 8b is a side view of the alternative embodiment folded into a compact storage position.

As shown in FIGS. 8a and 8b of the drawings, a hinge 26 may connect the lower frame 24 and the upper frame 22 in a pivotal manner for allowing folding of the chair frame 20 into a compact storage position. The legs of the chair frame 20 are also pivotally attached to the lower frame 24 of the chair frame 20 for folding into a compact storage position. One or more handles 28 are preferably attached to the chair frame 20 for allowing carrying of the present invention when folded into the storage position.

C. Seat

Figure 3:
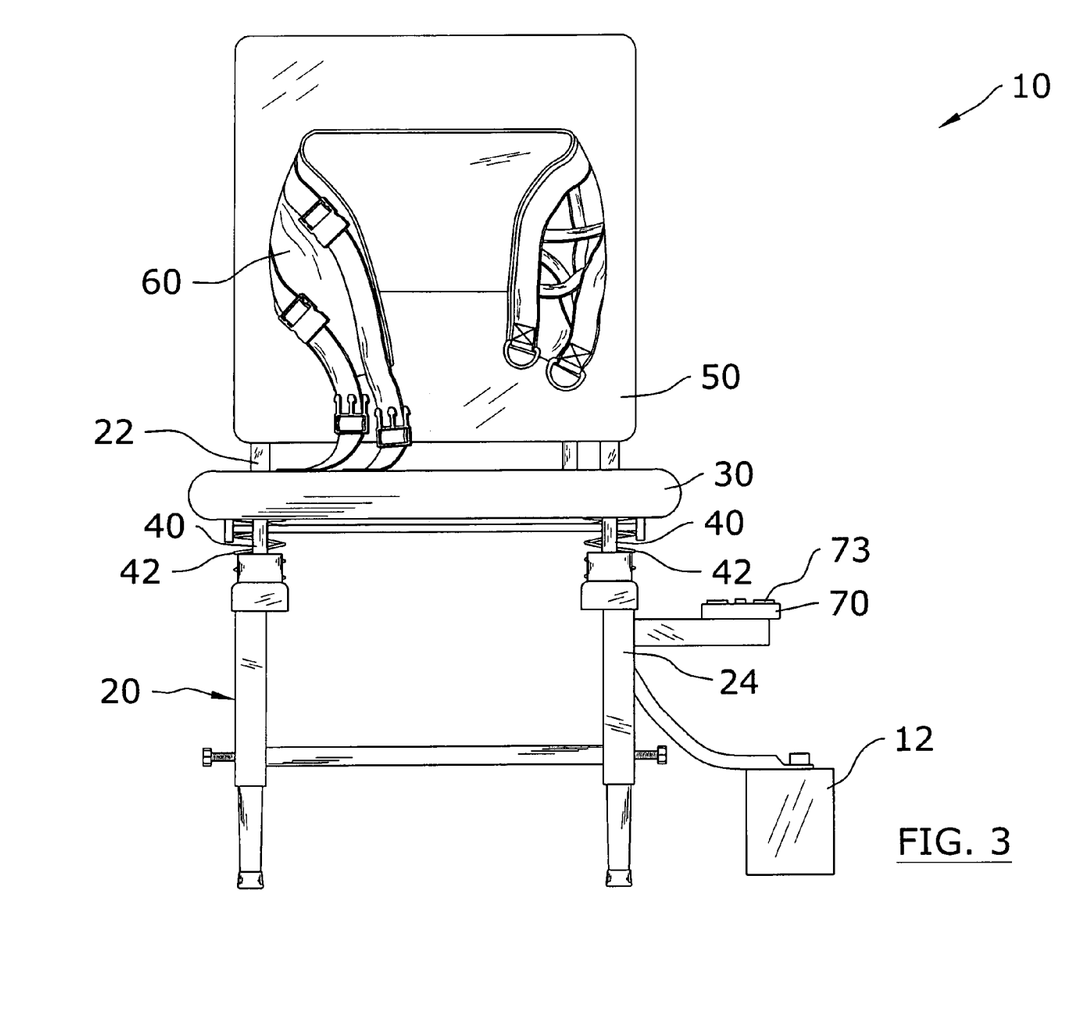
FIG. 3 is a front view of the present invention.
Figure 4:
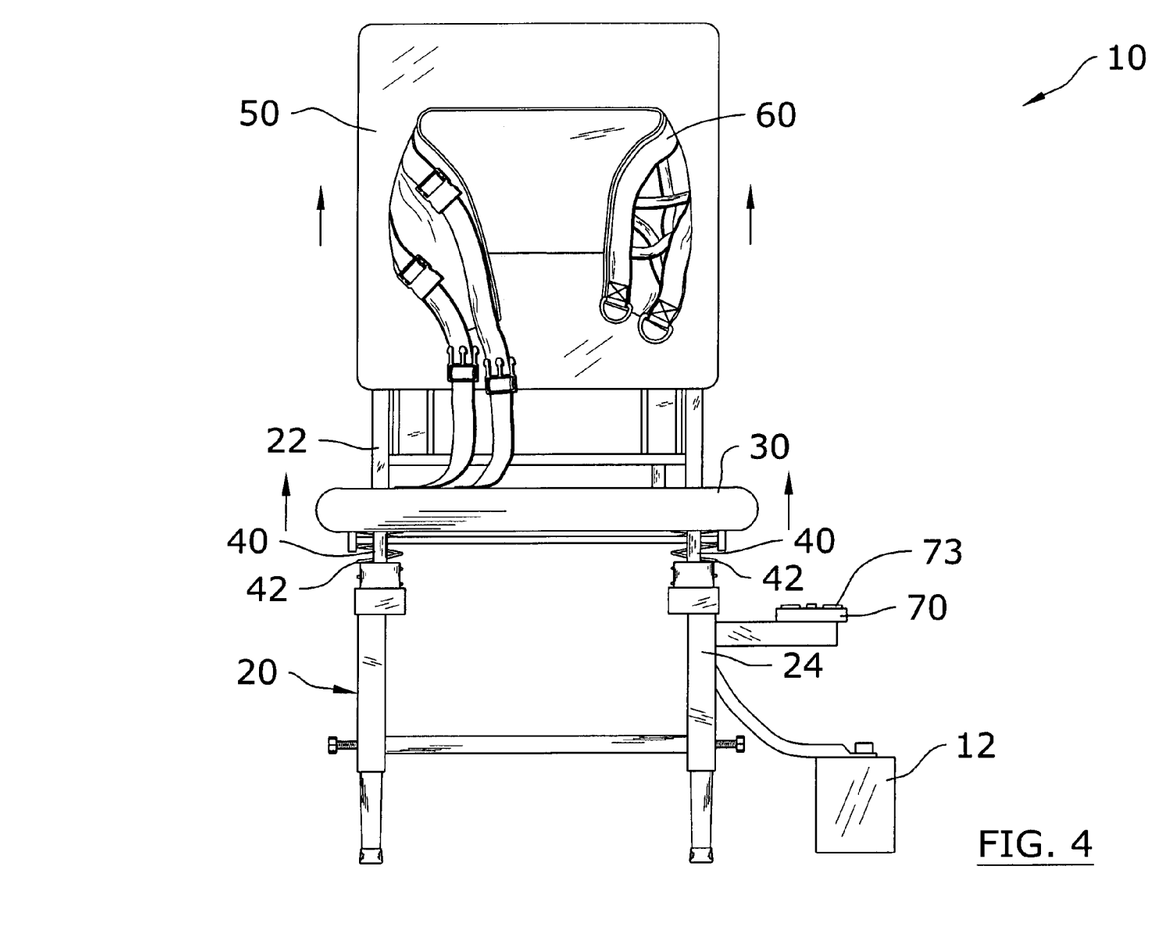
FIG. 4 is a front view of the present invention illustrating the backrest elevated.
Figure 5:
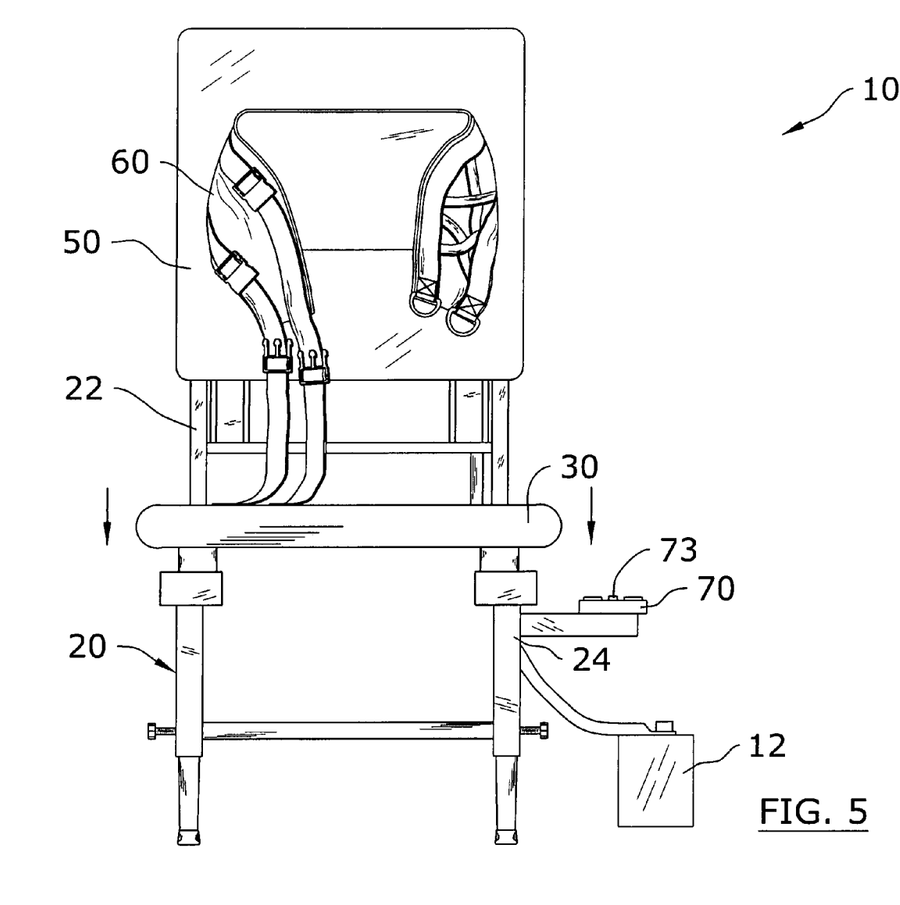
FIG. 5 is a front view of the present invention illustrating the seat lowered.
Figure 7A:
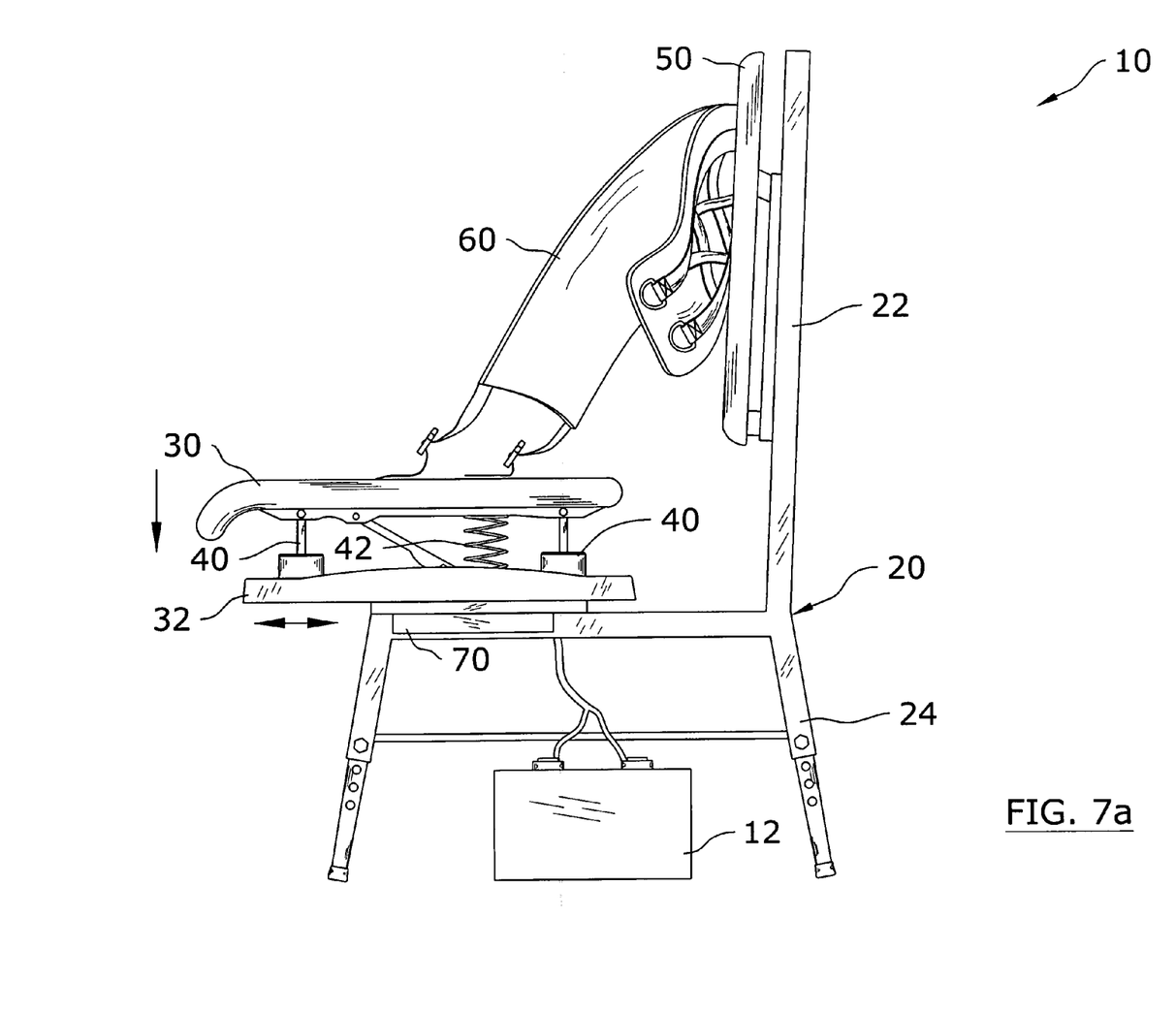
FIG. 7a is a side view of the present invention with the seat elevated and the backrest lowered.

As shown in FIGS. 2 and 7a of the drawings, a base 32 is preferably movably attached to the lower frame 24 in a horizontal manner. The base 32 may be attached to rails or other adjustable structures for allowing adjustment of the horizontal position of the base 32 and the seat 30. A guide arm may be attached between the seat 30 and the base 32 to provide additional stability to the seat 30 being supported by the actuators 40 as illustrated in FIG. 7a of the drawings. At least one actuator 40 is attached between the base 32 and the seat 30 for selectively elevating/lowering the seat 30 as desired as shown in FIGS. 3, 4 and 7a of the drawings.

The actuator 40 is preferably comprised of an electrically powered structure, however other structures may be utilized for the actuators 40 (e.g. hydraulic cylinders, etc.). The seat 30 is preferably comprised of a cushioned structure. At least one compression spring 42 is preferably attached between the seat 30 and the base 32 for providing an upward force to the seat 30 as best illustrated in FIGS. 3, 4 and 7a of the drawings. The compression spring 42 provides a balancing force to the seat 30 to help reduce movement of the seat 30 during operation of the present invention.

A scale 72 is positioned within the seat 30 (or on top of the seat 30) and is in communication with the control unit 70 for providing feedback to the individual regarding the amount of traction being applied. The scale 72 provides an initial weight of the individual to the control unit 70 so the control unit 70 can determine the amount of traction being applied to the individual base 32d upon the reduction in the force applied to the scale 72.

D. Backrest

Figure 6:
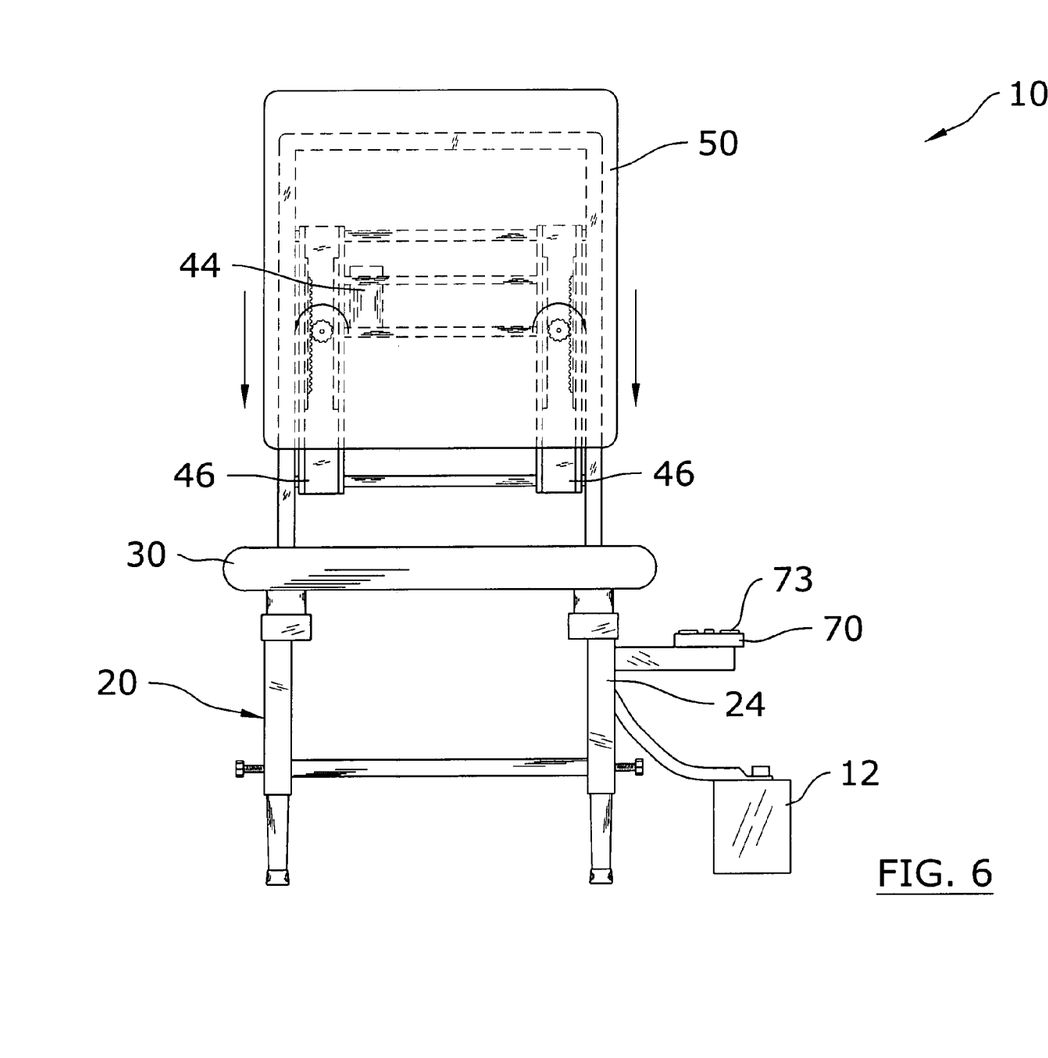
FIG. 6 is a front view of the present invention illustrating the drive structure for elevating/lowering the backrest.

FIGS. 1 through 7c illustrate the backrest 50 movably attached to the upper frame 22 in a vertical manner. A plurality of support rails 46 are preferably attached between the upper frame 22 and the backrest 50 for supporting the backrest 50 in a vertically movable position as shown in FIG. 6 of the drawings. A motor 44 is attached to the upper frame 22 and is mechanically connected to the backrest 50 in a rack and pinion configuration for elevating/lowering the backrest 50 as shown in FIG. 6 of the drawings. Alternatively, an actuator 40 may be attached between the backrest 50 and the upper frame 22 for manipulating the position of the backrest 50. The backrest 50 is preferably comprised of a cushioned structure.

Figure 7B:
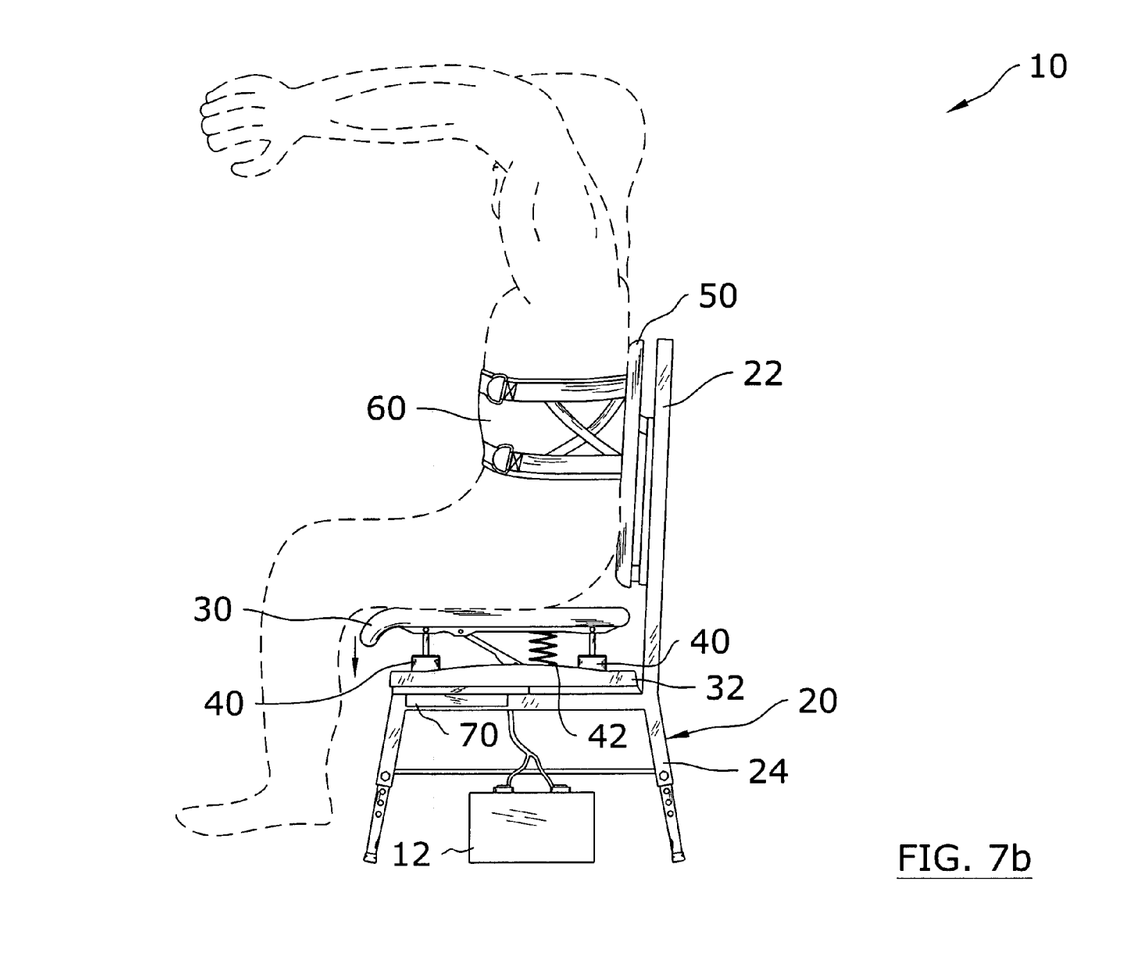
FIG. 7b is a side view of the present invention with the individual sitting upon the seat and secured within the harness.
Figure 7C:
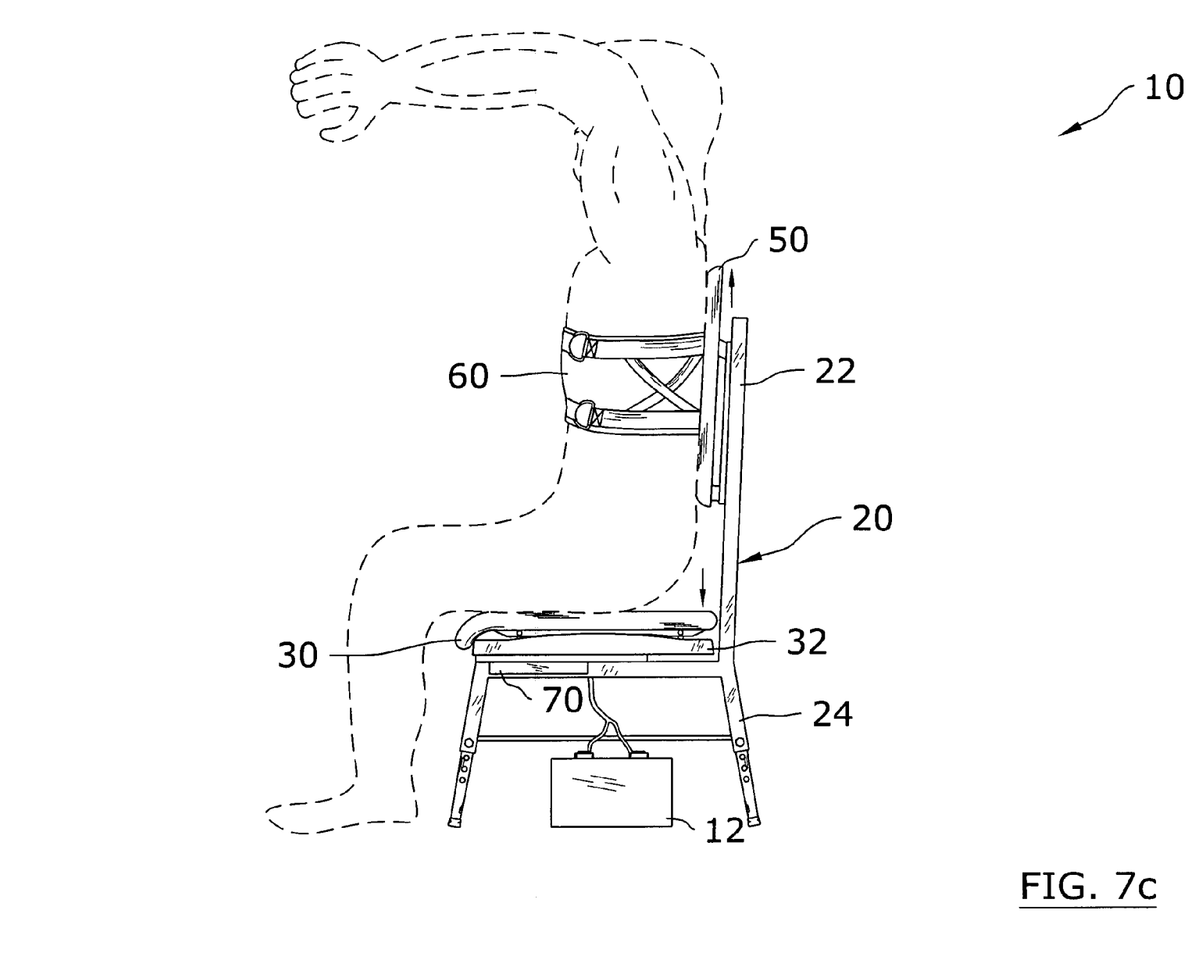
FIG. 7c is a side view of the present invention with the seat lowered and the backrest raised thereby placing the individual's back in traction.

A harness 60 is attached to the backrest 50 for securing an individual to the backrest 50 as shown in FIGS. 1 through 5 and 7a through 7c of the drawings. The harness 60 may be comprised of various structures capable of adjustably attaching about the upper torso of an individual as best illustrated in FIGS. 7b and 7c of the drawings. The harness 60 may be comprised of various structures commonly found capable of attaching the upper torso of an individual to the backrest 50 in a secure and snug manner to limit the amount of movement of the upper torso with respect to the backrest 50 when the backrest 50 is elevated.

E. Control Unit

Figure 9:
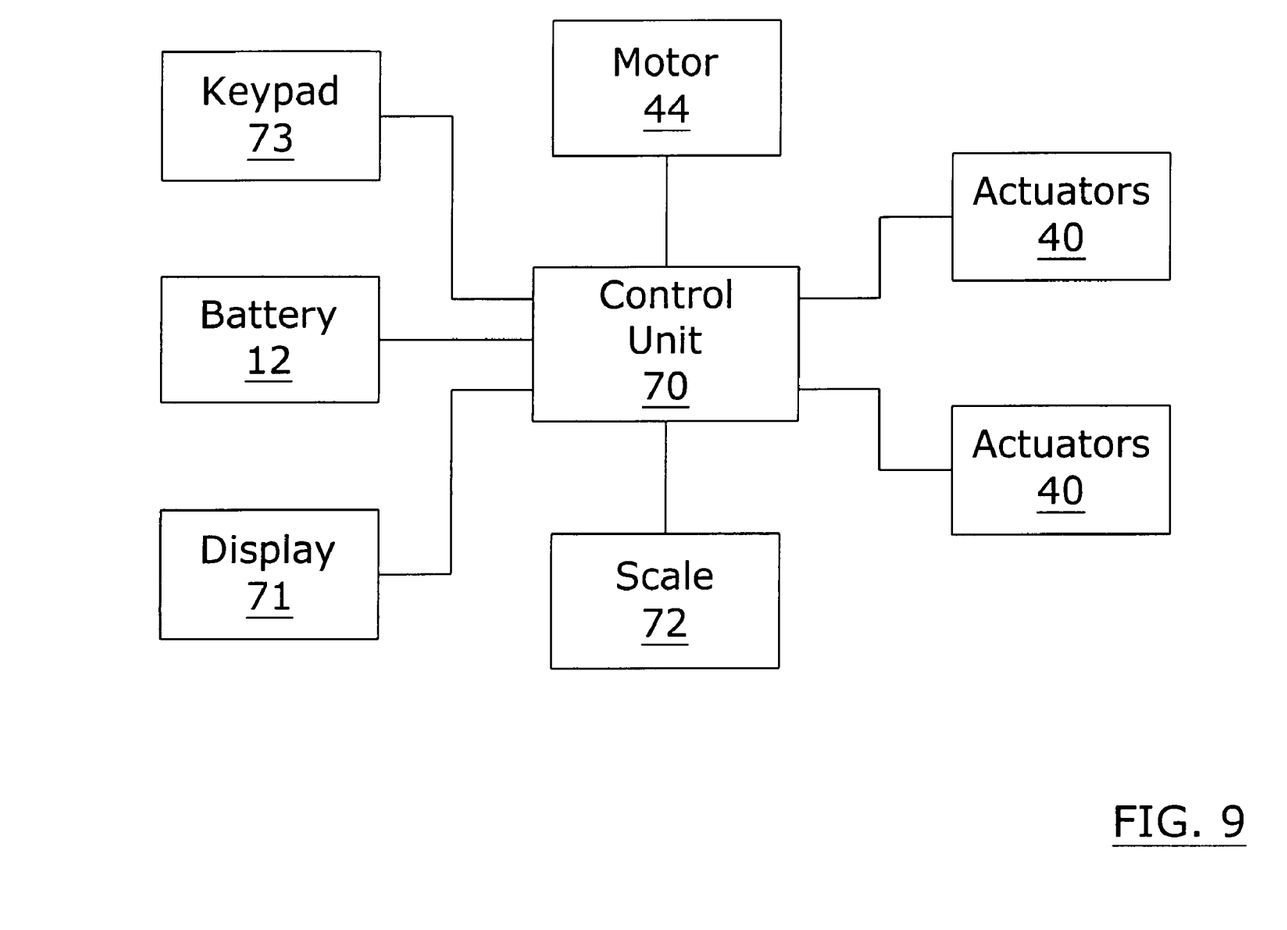
FIG. 9 is a block diagram of the present invention.

The control unit 70 is in communication with the actuators 40 and the motor 44 for controlling the same as shown in FIG. 9 of the drawings. The control unit 70 is also in communication with the scale 72 for calculating the amount of traction force (calculable in pounds, kilograms, percentage of body weight, etc.). The control unit 70 also preferably includes a display 71 that shows the amount of traction being applied to the individual as shown in FIGS. 1 and 9 of the drawings.

A keypad 73 is preferably in communication with the control unit 70 for allowing the individual to control the position of the seat 30 and the backrest 50 as further shown in FIGS. 1 and 9 of the drawings. A battery 12 or other commonly utilized power source (e.g. AC power) is electrically connected to the control unit 70 for providing electrical power to the present invention for manipulating the actuators 40 and the motor 44.

The control unit 70 may be comprised of any programmable electronic device capable of performing data calculations and controlling external equipment. The control unit 70 is preferably mounted to the chair frame 20 in a convenient to access location, but the control unit 70 may also be comprised of a portable unit.

F. Operation of Invention

In use, the individual first lowers the backrest 50 to the lowered position and then raises the seat 30 to the raised position as illustrated in FIGS. 3 and 7a of the drawings. The individual then sits upon the seat 30 and then secures the harness 60 about their upper torso (preferably below their arms) as illustrated in FIG. 7b of the drawings. The individual then manipulates the keypad 73 of the control unit 70 to raise the backrest 50 upwardly as shown in FIG. 7c of the drawings. The backrest 50 is capable of being elevated up to at least six inches to provide a desired level of traction to the lower back of the individual. The individual may also cause the seat 30 to lower to increase the amount of traction if the backrest 50 elevating doesn't provide the desired level of traction. It is desirable to achieve a traction amount equal to approximately forty-percent of the individual's gross body weight. The individual then remains in the traction state for a period of time to relieve the pressure and pain upon the lower back. When the individual is finished, they simply manipulate the keypad 73 of the control unit 70 to cause the backrest 50 to lower and the seat 30 to elevate thereby reducing the traction. The individual then releases the harness 60 and is then able to leave the present invention.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

I claim:

1. A traction chair system, comprising:
   a chair frame;
   a seat;
   at least one actuator attached between said chair frame and said seat for selectively elevating/lowering said seat;
   a backrest;
   a harness attached to said backrest for securing an individual to said backrest;
   a motor attached to said chair frame and mechanically connected to said backrest for elevating/lowering said backrest; and
   a control unit in communication with said at least one actuator and said motor for controlling the same;
   a scale positioned within said seat and in communication with said control unit for providing feedback to the individual regarding the amount of traction being applied.

2. The traction chair system of claim 1 wherein said control unit includes a display that shows the amount of traction being applied.

3. The traction chair system of claim 2 wherein said control unit includes a keypad for allowing the individual to control the position of said seat and said backrest.

4. The traction chair system of claim 1, including at least one compression spring attached between said seat and said chair frame for providing an upward force to said seat.

5. The traction chair system of claim 1, wherein said at least one actuator is comprised of a plurality of actuators.

6. The traction chair system of claim 1, including a plurality of support rails attached between said chair frame and said backrest for supporting said backrest in a vertically movable position.

7. The traction chair system of claim 6 wherein said motor and said support rails are comprised of a rack and pinion configuration.

8. The traction chair system of claim 1, wherein said chair frame includes a lower frame for supporting said seat and an upper frame extending upwardly from said lower frame for supporting said backrest.

9. The traction chair system of claim 8 wherein said upper frame is pivotally attached to said lower frame.

10. A traction chair system, comprising:
    a chair frame having an upper frame extending from a lower frame;
    a base movably attached to said lower frame in a horizontal manner;
    a seat;
    at least one actuator attached between said base and said seat for selectively elevating/lowering said seat;
    a backrest;
    a harness attached to said backrest for securing an individual to said backrest;
    a motor attached to said upper frame and mechanically connected to said backrest for elevating/lowering said backrest; and
    a control unit in communication with said at least one actuator and said motor for controlling the same.

11. The traction chair system of claim 10 including a scale positioned within said seat and in communication with said control unit for providing feedback to the individual regarding the amount of traction being applied.

12. The traction chair system of claim 11 wherein said control unit includes a display that shows the amount of traction being applied.

13. The traction chair system of claim 12 wherein said control unit includes a keypad for allowing the individual to control the position of said seat and said backrest.

14. The traction chair system of claim 10 including at least one compression spring attached between said seat and said chair frame for providing an upward force to said seat.

15. The traction chair system of claim 10 wherein said at least one actuator is comprised of a plurality of actuators.

16. The traction chair system of claim 10 including a plurality of support rails attached between said upper frame and said backrest for supporting said backrest in a vertically movable position.

17. The traction chair system of claim 16 wherein said motor and said support rails are comprised of a rack and pinion configuration.

18. The traction chair system of claim 10 wherein said upper frame is pivotally attached to said lower frame.

19. A traction chair system, comprising:
    a chair frame having an upper frame extending from a lower frame;
    a base movably attached to said lower frame in a horizontal manner;
    a seat;
    at least one actuator attached between said base and said seat for selectively elevating/lowering said seat;
    a backrest;
    a plurality of support rails attached between said upper frame and said backrest for supporting said backrest in a vertically movable position;
    a harness attached to said backrest for securing an individual to said backrest;
    a motor attached to said upper frame and mechanically connected to said backrest in a rack and pinion configuration for elevating/lowering said backrest;
    a control unit in communication with said at least one actuator and said motor for controlling the same, wherein said control unit includes a display that shows the amount of traction being applied and a keypad for allowing the individual to control the position of said seat and said backrest;
    a scale positioned within said seat and in communication with said control unit for providing feedback to the individual regarding the amount of traction being applied; and
    at least one compression spring attached between said seat and said base for providing an upward force to said seat.

* * * * *